(12) United States Patent
Ishii et al.

(10) Patent No.: US 6,844,744 B2
(45) Date of Patent: Jan. 18, 2005

(54) SURFACE SHAPE RECOGNITION SENSOR AND METHOD OF MANUFACTURING THE SAME

(75) Inventors: Hiromu Ishii, Kanagawa (JP); Shouji Yagi, Kanagawa (JP); Katsuyuki Machida, Kanagawa (JP); Hakaru Kyuragi, Tokyo (JP)

(73) Assignee: Nippon Telegraph and Telephone Corporation, Tokyo (JP)

( * ) Notice: Subject to any disclaimer, the term of this patent is extended or adjusted under 35 U.S.C. 154(b) by 42 days.

(21) Appl. No.: 10/359,664

(22) Filed: Feb. 5, 2003

(65) Prior Publication Data

US 2003/0173982 A1 Sep. 18, 2003

(30) Foreign Application Priority Data

Feb. 8, 2002 (JP) ........................................ 2002-032051

(51) Int. Cl.[7] .......................... G01R 27/26; H01L 29/82
(52) U.S. Cl. ........................................ 324/686; 257/414
(58) Field of Search ................................. 324/653, 686, 324/658, 649, 600, 663, 177, 178, 207.13, 207.14, 76.11, 219, 239, 241, 242, 243, 515, 519, 530, 548, 661; 257/414, 415, 432, 434, 448, 459, 295, 534; 428/1.3, 195.1, 323, 336, 212, 408, 690; 382/124, 312; 438/3, 64, 458, 586, 763, 687, 690

(56) References Cited

U.S. PATENT DOCUMENTS

| | | | | |
|---|---|---|---|---|
| 5,200,230 A | * | 4/1993 | Poullos et al. | 427/8 |
| 5,618,617 A | * | 4/1997 | Uchida et al. | 428/323 |
| 5,695,834 A | * | 12/1997 | Sheets | 428/1.3 |
| 6,060,756 A | * | 5/2000 | Machida et al. | 257/415 |
| 6,248,655 B1 | * | 6/2001 | Machida et al. | 438/597 |
| 6,251,500 B1 | * | 6/2001 | Varga et al. | 428/195.1 |
| 6,285,033 B1 | * | 9/2001 | Matsumoto | 250/548 |
| 6,310,024 B1 | * | 10/2001 | Gill et al. | 510/247 |
| 6,399,994 B2 | * | 6/2002 | Shobu | 257/414 |
| 6,438,257 B1 | * | 8/2002 | Morimura et al. | 382/124 |
| 6,518,083 B2 | * | 2/2003 | Sato et al. | 438/50 |
| 6,556,935 B2 | * | 4/2003 | Morimura et al. | 702/104 |
| 6,714,666 B1 | * | 3/2004 | Morimura et al. | 382/124 |
| 6,727,561 B2 | * | 4/2004 | Sato et al. | 257/414 |
| 2001/0028074 A1 | * | 10/2001 | Kutsunai et al. | 257/295 |
| 2002/0121909 A1 | * | 9/2002 | Sato et al. | 324/686 |
| 2003/0016024 A1 | * | 1/2003 | Teranuma et al. | 324/519 |
| 2003/0085125 A1 | * | 5/2003 | Prohaska et al. | 204/424 |

FOREIGN PATENT DOCUMENTS

| | | | | |
|---|---|---|---|---|
| JP | 10-269340 A | | 10/1998 | |
| JP | 2001214055 A | * | 8/2001 | ........... C08L/79/04 |

OTHER PUBLICATIONS

Fourth–page article of the third evening edition of the Asahi Shimbun published by Tokyosha, Aug. 22, 1999.

* cited by examiner

*Primary Examiner*—N. Le
*Assistant Examiner*—Hoai-An D. Nguyen
(74) *Attorney, Agent, or Firm*—Blakely Sokoloff Taylor & Zafman

(57) ABSTRACT

A surface shape recognition sensor of this invention has a surface protective film having a hydrophobic property on an insulating protective film which is made of an insulator and formed to cover a sensor electrode, and includes at least a ground electrode which is formed on the substrate such that the ground electrode is partly exposed on the surfaces of the insulating protective film and surface protective film so as to be insulated/isolated from the sensor electrode and come into contact with the surface of a detection target. This sensor prevents fingerprint residues from easily remaining and improves tamper resistance.

13 Claims, 4 Drawing Sheets

SURFACE SHAPE RECOGNITION SENSOR AND METHOD OF MANUFACTURING THE SAME

BACKGROUND OF THE INVENTION

The present invention relates to a surface shape recognition sensor used to sense a surface shape having fine recesses and projections such as human fingerprints and animal's noseprints and a method of manufacturing the sensor and, more particularly, to a surface shape recognition sensor whose recognition surface is protected and a method of manufacturing the sensor.

With the recent proliferation of the Internet, a great deal of attention has been paid to the importance of authentication. Biometrics, in which authentication is performed by measuring/evaluating biological characteristics, has greatly advanced as a technical field of authentication. Authentication using fingerprints, in particular, has been vigorously studied as an authentication means for measuring/evaluating a physical characteristic that cannot be easily changed. In order to perform authentication by using a fingerprint, the fingerprint is read. Systems for reading fingerprints include various systems such as optical systems and capacitive systems. Except for some of the optical systems, when a fingerprint is to be read, the finger generally touches a fingerprint sensor surface.

In a system in which the fingers are made to touch a fingerprint sensor surface, fingerprint residues including sebum remain on the sensor. With the recent increasing orientation toward cleanliness, many users hate to touch the sensor surface, and hence it is required to take measures against this problem (e.g., fourth-page article of the third evening edition of the Asahi Shimbun published by Tokyosha, Aug. 22, 1999). In addition, a fingerprint shape can be easily collected and reproduced from a fingerprint residue left on the sensor surface by the so-called powder method using aluminum powder like that executed by a crime laboratory. From the viewpoint of tamper resistance as well, it is necessary to take measures against the problem.

Furthermore, fingerprint residues interfere as noise with authentication, and hence degrade the authentication performance of the fingerprint sensor. Under the present circumstances, cleaning and wiping the sensor surface are only measures against these problems. With such measures, however, for example, the sensor cannot be continuously used, thus prosing a serious problem.

SUMMARY OF THE INVENTION

It is, therefore, the main object of the present invention to suppress a deterioration in cleanliness on the detection surface of a surface shape recognition sensor such as a fingerprint sensor used for, for example, authentication due to residues such as fingerprint residues left on the detection surface which a detection target such as a finger touches, and prevent fingerprint residues from easily remaining, thereby improving tamper resistance and suppressing a deterioration in detection precision with respect to a surface shape such as a fingerprint.

In order to achieve the above object, according to one aspect of the present invention, there is provided a surface shape recognition sensor comprising a plurality of sensor electrodes arranged in the same plane on a substrate so as to be insulated/isolated from each other, an insulating protective film which is made of an insulator and formed to cover the sensor electrodes, capacitance detection means for detecting a capacitance formed by the sensor electrode, a surface protective film which has a hydrophobic property and is formed on the insulating protective film, and a ground electrode which is formed on the substrate such that the ground electrode is partly exposed on surfaces of the insulating protective film and the surface protective film so as to be insulated/isolated from the sensor electrode and come into contact with a surface of a detection target, wherein the capacitance detection means is configured to detect a capacitance between the ground electrode and each of the sensor electrodes.

This arrangement restrains substances existing on the surface of a detection target from remaining on the surface of the surface protective film upon contact of the detection target with the surface protective film.

According to another aspect of the present invention, there is provided a method of manufacturing a surface shape recognition sensor including at least a plurality of sensor electrodes arranged in the same plane on a substrate so as to be insulated/isolated from each other, an insulating protective film which is made of an insulator and formed to cover the sensor electrodes, capacitance detection means for detecting a capacitance formed by the sensor electrode, and a connection terminal exposed on a surface of the insulating protective film, wherein a surface protective film made of a specific material, which forms a film having a hydrophobic property, is formed on the insulating protective film by coating the film with a coating solution in which the specific material is dissolved.

By manufacturing the sensor in this manner, a surface protective film is not easily formed on the upper surface (exposed surface) of a connection terminal made of gold or the like.

DESCRIPTION OF THE PREFERRED EMBODIMENTS

The embodiments of the present invention will be described in detail below with reference to the accompanying drawings.

[First Embodiment]

Figure 1A:
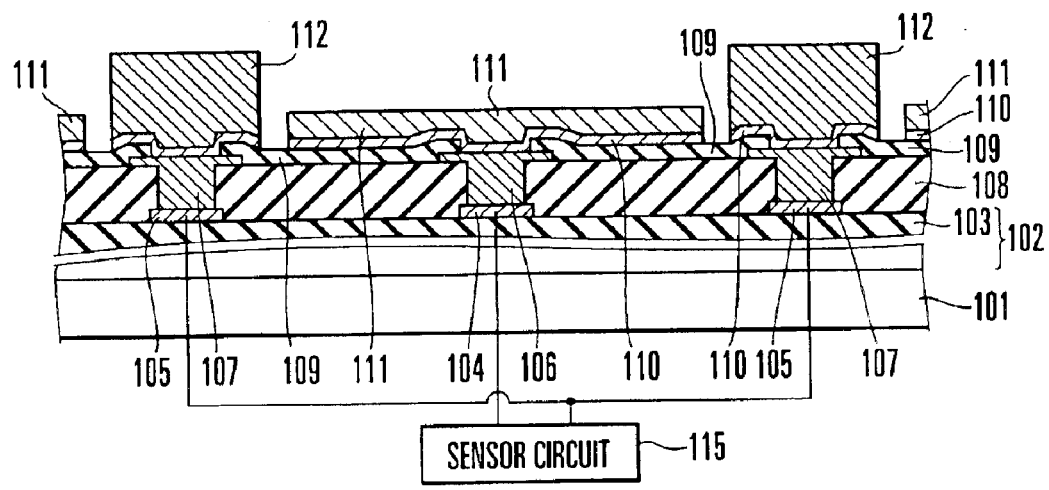
FIG. 1A is a schematic sectional view showing part of the structure of a surface shape recognition sensor according to the first embodiment of the present invention.
Figure 1B:
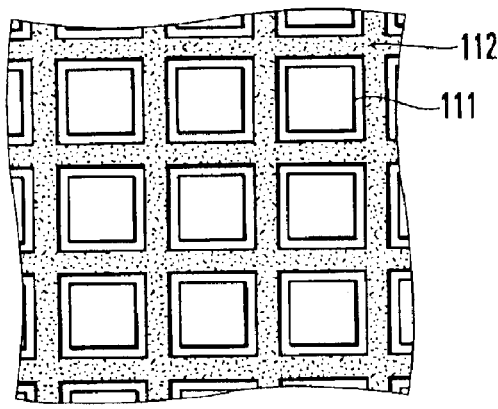
FIG. 1B is a plan view showing part of the structure of the surface shape recognition sensor according to the first embodiment of the present invention.
Figure 1C:
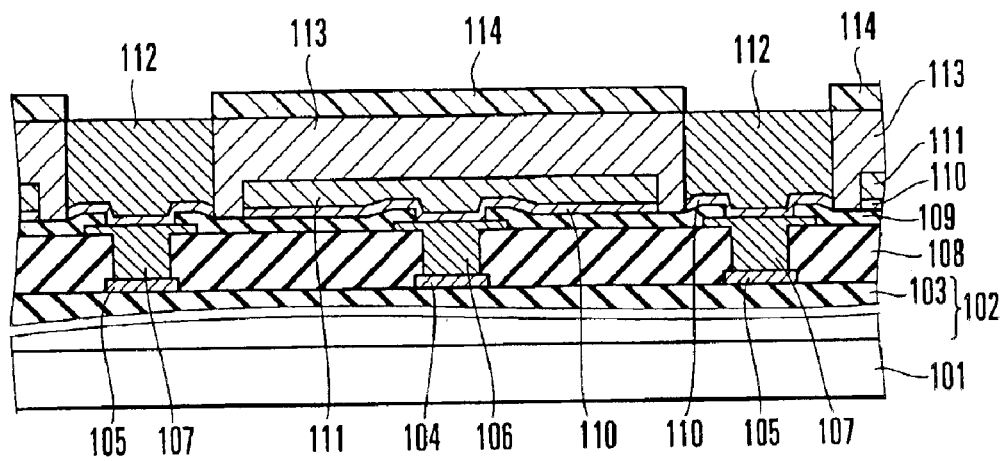
FIG. 1C is a schematic sectional view showing part of the structure of the surface shape recognition sensor according to the first embodiment of the present invention.

The first embodiment of the present invention will be described first. FIGS. 1A, 1B, and 1C explain a method of manufacturing a surface shape recognition sensor (sensor chip) according to this embodiment. The state shown in FIG. 1A will be described first. First of all, a multilevel interconnection layer 102 is formed on a semiconductor substrate 101 made of, for example, silicon. The uppermost layer of the multilevel interconnection layer 102 is covered with an insulating film 103, and interconnections 104 and 105 are formed on the insulating film 103.

The multilevel interconnection layer 102 is formed from a plurality of elements such as MOS transistors (not shown) and a plurality of interconnections (not shown) which connect the elements, and forms a sensor circuit 115 and the like. The interconnections 104 and 105 are connected to these circuits. Note that an illustration of the sensor circuit 115 is omitted in subsequent drawings, e.g., FIGS. 1C, 3, and 4.

The interconnections 104 and 105 are covered with an interlayer dielectric film 108. Connection electrodes 106 and 107 extending through the through holes formed in portions of the interlayer dielectric film 108 are connected to the interconnections 104 and 105. The respective interconnections and connection electrodes may be formed by patterning using a known film forming technique, photolithographic technique, or etching technique. An insulating film 109 is formed on the interlayer dielectric film 108 such that the central portions of the upper portions of the connection electrodes 106 and 107 are exposed.

In this state, a copper film having a thickness of about 0.1 $\mu$m is formed on the insulating film 109 and the exposed portions of the connection electrodes 106 and 107 by, for example, sputtering. A resist pattern having an opening portion with a square shape in plan which is centered on the connection electrode 106 is formed on the connection electrode 106 and insulating film 109. A gold film having a thickness of about 1 $\mu$m is formed on the copper film exposed in this opening portion by electrolytic plating or the like.

The above resist pattern is removed, and a new resist pattern having opening portions in a lattice pattern is formed on the plurality of connection electrodes 107, and a gold film having a thickness of about 3 $\mu$m is formed on the copper film exposed in the lattice pattern by electrolytic plating or the like. The resist pattern is then removed.

With this process, a gold pattern with a square shape in plan is formed on the upper portion of the connection electrode 106, and a gold lattice pattern is continuously formed on the upper portions of the plurality of connection electrodes 107. The lower copper film is removed by etching using the gold pattern formed in this manner as a mask, thereby electrically isolating the lattice pattern portion from the portion with a square shape in plan.

As a result, a square sensor electrode 111 connected to the connection electrode 106 is formed on the insulating film 109, and a ground electrode 112 connected to the connection electrodes 107 is formed.

As shown in FIG. 1B, sensor electrodes 111 are so formed as to be isolated from each other on the sensor chip, and the ground electrode 112 in a lattice pattern is formed such that the sensor electrodes 111 are arranged in squares.

When the sensor electrodes 111 and ground electrode 112 are formed in the above manner, an insulating protective film 113 serving as a capacitance film is formed on the sensor electrode 111, as shown in FIG. 1C. The insulating protective film 113 is formed such that the sensor electrode 111 is covered with the film but the upper portion of the ground electrode 112 is exposed. For example, the insulating protective film 113 can be formed by forming a polyimide film made of a polyimide material included in CRC-8300 series available from SUMITOMO BAKELITE to a thickness of about 3 $\mu$m by a coating technique and setting the film by heating it at about 300° C.

After the insulating protective film 113 is formed in this manner, a fluoroplastic film (surface protective film) 114 made of a fluorocarbon material (specific material) is formed on the insulating protective film 113. As a fluorocarbon material, for example, AF 1600 (Teflon®) available from DuPont can be used.

A method of forming the fluoroplastic film 114 will be described below. First of all, AF 1600 is dissolved in Fluorinert FC-75 (solvent) available from 3M to form a saturated solution of AF 1600 at a room temperature of 23.5° C. This saturated solution will be referred to as a Teflon® saturated solution hereinafter.

When a saturated solution is formed in the above manner, this saturated solution is applied onto the insulating protective film 113 by spin coating. The resultant structure is heated in an atmosphere at 170° C. for 5 min. The resultant structure is then annealed in a nitrogen atmosphere at 300° C. for 1 hr. As a result, the fluoroplastic film 114 can be formed, as shown in FIG. 1C. At this time, as will be described later, since a coating film of a fluoroplastic film is thin and exhibits poor adhesion on gold, the fluoroplastic film 114 is hardly formed on the ground electrode 112 made of gold.

Note that a plurality of sensor chips (surface shape recognition sensors) are simultaneously formed on the semiconductor substrate 101 which is a semiconductor wafer, detection surfaces formed from the plurality of sensor electrodes 111 are formed on the respective sensor chips, and the detection surfaces are protected by the insulating protective film 113 and fluoroplastic film 114. FIG. 1C shows some of these components, i.e., schematically shows part of the structure of the surface shape recognition sensor. The sensor circuit 115 shown in FIG. 1 is connected to the sensor electrode 111 through the interconnection 104 and connection electrode 106, and is also connected to the ground electrode 112 through the interconnections 105 and connection electrodes 107.

Various types of connection terminals are formed on the surface of the sensor chip. For example, the ground electrode 112 is formed on a detection surface, and an external connection terminal is formed on an outer peripheral portion of the sensor chip. In this state, when a fluoroplastic film is formed by only spin coating as described above, the above connection terminals are also covered with the fluoroplastic film. A fluoroplastic film formed on connection terminals will be described below.

First of all, the following samples were formed. A coating solution obtained by mixing a Teflon® saturated solution with Fluorinert FC-75 (solvent) at a mixing ratio of 3:1 or 1:1 was applied onto a substrate with each of underlayers in various states by spin coating at 1,000 rmp. The resultant structure was heated in an atmosphere at 170° C. for 5 min. The resultant structure was then annealed in a nitrogen atmosphere at 300° C. for 1 hr, thereby forming a Teflon® film. Table 1 shows the result of obtaining the thickness of each Teflon® film formed in this manner by in-depth analysis based on Auger electron spectroscopy.

TABLE 1

| Underlayer | Mixing ratio | |
| --- | --- | --- |
|  | 3:1 | 1:1 |
| gold | 1 nm or less | about 10 nm |
| polyimide | 12 nm | 200 to 300 nm |
| silicon | 12 nm | 200 to 300 nm |
| silicon oxide film | 12 nm | 200 to 300 nm |

As is obvious from Table 1, the coating films greatly vary in thickness at the different mixing ratios. Although the number of revolutions in coating is set to 1,000 rpm in Table 1, the film thickness hardly changes even if the number of revolutions in coating is changed between 500 to 5,000 rpm.

It is apparent from Table 1 that coating films greatly vary in thickness depending on the underlayer materials. As is obvious, in particular, a film is not formed much on gold. Although the details of a cause of such differences are not clear from a molecular or atomic point of view, it is conjectured that such differences are based on the differences in wettability and surface energy between the Teflon® saturated solution and the underlayers.

When the adhesion of each formed coating film (Teflon® film) with respect to each underlayer is performed by a Scotch tape test in addition to the above test, the coating film formed on the gold underlayer peels off, but the coating films on the substrates with the underlayers made of other materials keep adhering without peeling off. It is therefore obvious that the coating film on gold is thin and exhibit poor adhesion.

It is also evident from the following experiment result that the adhesion of the Teflon® film on gold is poor. After the above Teflon® saturated solution is applied onto a substrate with a gold underlayer, the electric resistance of the substrate is measured through the coating film by using a tester. In this case, a resistance can be measured in spite of the existence of the Teflon® film which is a nonconductor. In contrast to this, when the Teflon® film is formed on a silicon substrate generally exhibiting several kΩ, the measured resistance becomes infinite.

These results indicate that the Teflon® film formed on gold peels upon contact of the probe of the tester to allow intermetallic connection with the probe. This property of the Teflon® film remains unchanged even if the underlayer is made of stainless steel. On a substrate with a stainless steel underlayer, only a Teflon® film with poor adhesion can be formed. The above-described property of a Teflon® film is very effective in forming the fluoroplastic film 114 on the surface shape recognition sensor according to this embodiment as shown in FIG. 1C, as will be described next.

A detection surface has the ground electrode 112, and for example, static electricity generated when the finger touches the detection surface flows in the ground electrode 112. This protects circuit elements such as the sensor circuits 115 simultaneously formed on the semiconductor substrate 101 against electrostatic breakdown.

If the upper surface of the ground electrode 112 is covered with the fluoroplastic film 114, the above removal of static electricity cannot be done. As described above, however, the fluoroplastic film 114 is not formed on the upper surface (exposed surface) of the ground electrode 112. According to the surface shape recognition sensor in FIG. 1C, therefore, static electricity can be removed through the ground electrode 112.

The above surface shape recognition sensor (sensor chip) has a plurality of sensor electrodes 111 arranged in the form of a matrix. For example, the plurality of sensor electrodes 111 are arranged at 150-μm intervals to form the detection surface of the sensor chip. As described above, the sensor circuit is formed below the insulating film 103 on the semiconductor substrate 101 to detect the capacitance formed between the ground electrode 112 and each sensor electrode 111. For example, sensor circuits are prepared for the respective sensor electrodes 111, and an output from each sensor circuit is processed by a processing means constituted by other circuits (not shown). The resultant data is output as image data obtained by converting the capacitance formed by each sensor electrode 111 into halftone data.

Figure 2:
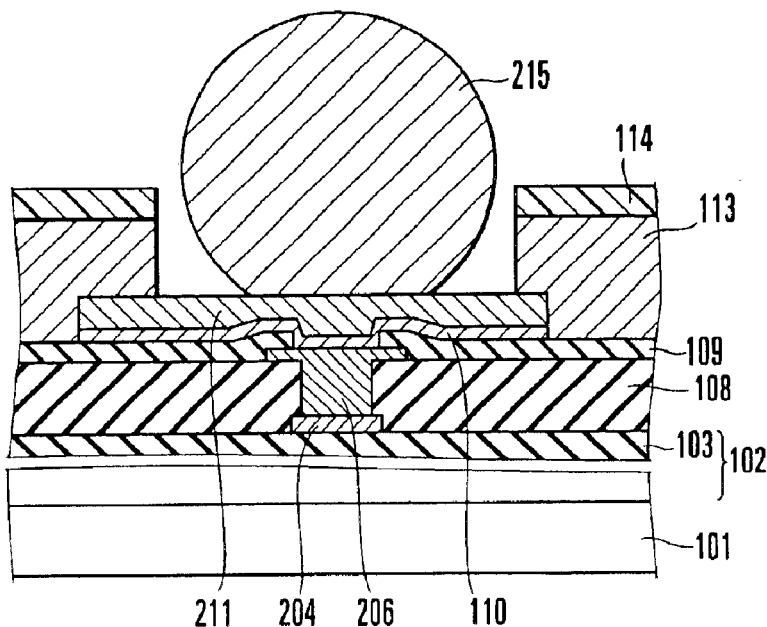
FIG. 2 is a schematic sectional view showing part of the structure of the surface shape recognition sensor according to the first embodiment of the present invention.

For example, as shown in FIG. 2, the sensor chip includes an external connection electrode 211 connected, through a connection electrode 206, to an interconnection 204 connected to any circuit formed on the multilevel interconnection layer 102, and a bump (external connection terminal) 215 made of gold on the external connection electrode 211. This sensor chip is mounted on a mount substrate (another substrate) by connecting the bump 215 to a connection portion of the mount substrate.

In this case, the above output image data is output to the mount substrate side through the external connection electrode 211 and bump 215. If, therefore, the fluoroplastic film 114 is formed on the insulating protective film 113 by spin coating, the fluoroplastic film 114 is also formed on the bump 215 formed on the sensor chip.

As described above, only a thin Teflon® film exhibiting poor adhesion can be formed on gold. Even if, therefore, the fluoroplastic film 114 is formed by spin coating, almost no film is formed on the bump 215.

For example, a Teflon® solution obtained by diluting a Teflon® saturated solution at a mixing ratio of 1:1 is applied, by spin coating at 1,000 rpm, to a wafer on which a plurality of sensor chips, on each of which components up to the insulating protective film 113 are formed, are simultaneously formed. The resultant structure is heated in an atmosphere at 170° C. and annealed in a nitrogen atmosphere at 300° C. for 30 min to form Teflon® films (fluoroplastic films 114).

Even if a Teflon® film is formed in this manner, a Teflon® film having a thickness of about 200 to 300 nm is formed, with good adhesion, on the insulating protective film 113 on which a plurality of sensor electrodes 111 are arranged, but almost no Teflon® film is formed on the bump 215. Even if a Teflon® film is formed on the bump 215, the film thickness is about 10 nm as indicated by Table 1 and the film is likely to peel off.

Even if, therefore, the fluoroplastic film 114 is formed by applying a Teflon® solution by spin coating, the fluoroplastic film 114 on the bump 215 need not be removed separately, and each sensor chip can be mounted on the mount substrate with electric connection being established. For example, the bump 215 can be connected to an inner lead used in TAB mounting in a short period of time by an eutectic reaction. In this case, the applied temperature instantaneously reaches 420° C., and it is expected that the thin fluoroplastic film 114 on the suture thread 214 is removed by this heat.

When a continuity test was actually conducted by bringing a test probe pin into contact with the bumps 215 for external connection on a wafer on which the plurality of sensor chips described above are formed (without cutting the wafer into chips), 80% chips were determined as defective due to contact failures at the bumps 215. When, however, the wafer was cut into chips and TAB mounting is executed, all the chips were determined as nondefective. This indicates that the thin fluoroplastic films 114 on the bumps 215 were removed at the time of TAB mounting.

The effect of the fluoroplastic film 114 formed by coating in the above manner will be described next. In this embodiment, the detection surface of the sensor chip is covered with the fluoroplastic film 114. Even if, therefore, the finger touches the detection surface, the detection surface becomes resistant to contamination and improves in tamper resistance. This effect originates from the fact that the fluoroplastic film 114 tends to repel moisture existing on the surface of the finger. In addition, it is conjectured that the fluoroplastic film 114 peels off on the molecular level. This is another factor for the above effect.

As described above, since the fluoroplastic film 114 peels off on the molecular level, it becomes thinner as the sensor chip is used, and eventually stops exhibiting the above effect. When a test of pressing a small rectangular plate against the surface of a sensor chip under 1 MPa was actually conducted as a durability test on a fingerprint sensor on which a fluoroplastic film was formed under the above conditions, it was confirmed that the residual fingerprint removing effect was lost after about 5,000 tests. Obviously, this durability test is a kind of accelerated test as compared with actual finger touching, and hence sufficient durability is ensured within a practical range.

In addition, selective coating of a fluoroplastic film and fingerprint residue removing property like those described above are not limited to the case wherein Teflon® is used. For example, even if another thin film having a hydrophobic property and lipophobic property, like a thin fluorocarbon film such as Cytop available from Asahi Glass, is used, the same effect as described above can be obtained. It is conjectured that this thin film also peels off by a thickness on molecular level upon touching of the finger (detection target). It is therefore conjectured that the effect owing to peeling of the thin film on molecular level can also be obtained.

As described above, the greatest characteristic feature of this embodiment is that the surface of a surface shape recognition sensor can be properly maintained by using a fluoroplastic film and the TAB scheme as a mounting scheme. It is obvious that this embodiment can solve the conventional problem that the surface of a sensor is susceptible to oil and moisture from the finger of a person, e.g., a fingerprint. In addition, if a photocatalyst such as titania is added to a fluoroplastic film, a further improvement in cleanliness and removal of residual fingerprints can be effectively attained owing to the antibacterial action and fat splitting effect.

[Second Embodiment]

Another embodiment of the present invention will be described next.

Figure 3:
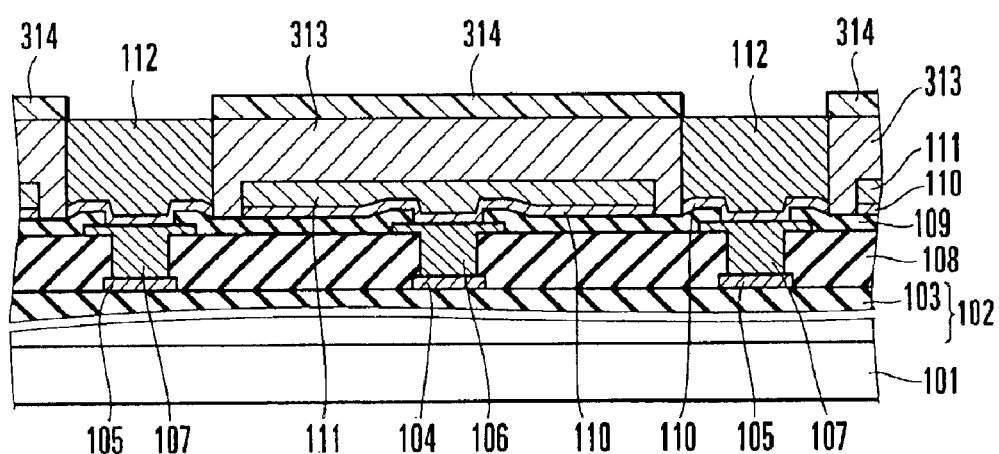
FIG. 3 is a schematic sectional view showing part of the structure of a surface shape recognition sensor according to the second embodiment of the present invention.

FIG. 3 schematically shows the structure of a surface shape recognition sensor according to this embodiment.

In the surface shape recognition sensor shown in FIG. 3, an insulating protective film 313 serving as a capacitance film formed on a sensor electrode 111 is made of silicon nitride, and a surface protective film 314 is made of polybenzoxazole. The insulating protective film 313 and surface protective film 314 in FIG. 3 are identical to those in FIG. 1C, and hence a description thereof will be omitted.

Figure 4:
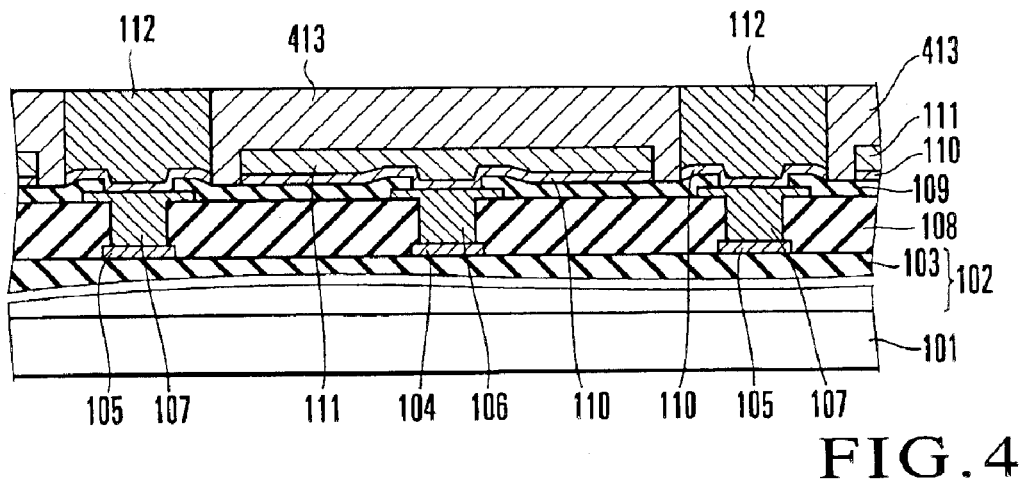
FIG. 4 is a schematic sectional view showing part of the structure of the surface shape recognition sensor according to the second embodiment of the present invention.

Assume that residues such as fingerprint residues left on the detection surface of the surface shape recognition sensor which a detection target touches are sebum. In this embodiment, since a polybenzoxazole film absorbs sebum, almost no fingerprint residues are left on the surface protective film 314. Polybenzoxazole also has a hydrophobic property (water repellency) so water-soluble foreign substances do not easily remain on the detection surface. Therefore, in this embodiment as well, the tamper resistance improves. Since a film having a thickness enough to fill the space between ground electrodes 112 can be easily formed by using a polybenzoxazole film, such a film can be formed as an insulating protective film 413, and its upper surface can be used as a surface protective film, as shown in FIG. 4. In this case, it can be said that the insulating protective film 413 is obtained by integrally forming the insulating protective film 313 and surface protective film 314 in FIG. 3.

[Third Embodiment]

Figure 5B:
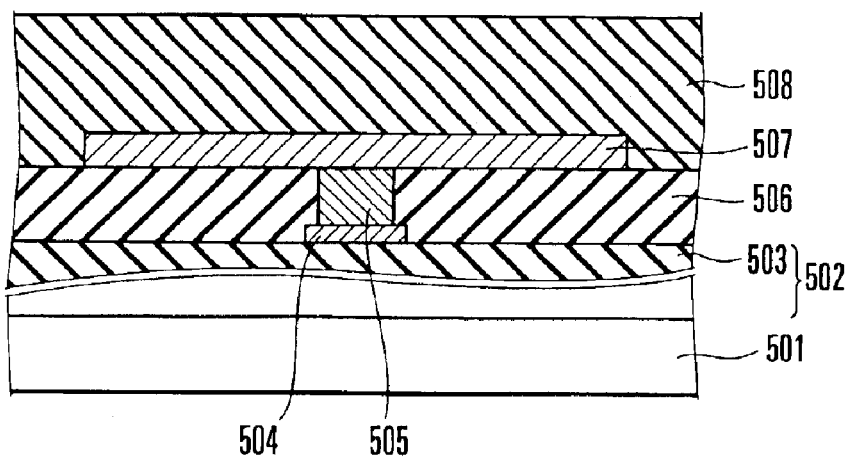
FIG. 5B is a sectional view for explaining a step following the step in FIG. 5A in the method of manufacturing a surface shape recognition sensor according to the third embodiment of the present invention.
Figure 6:
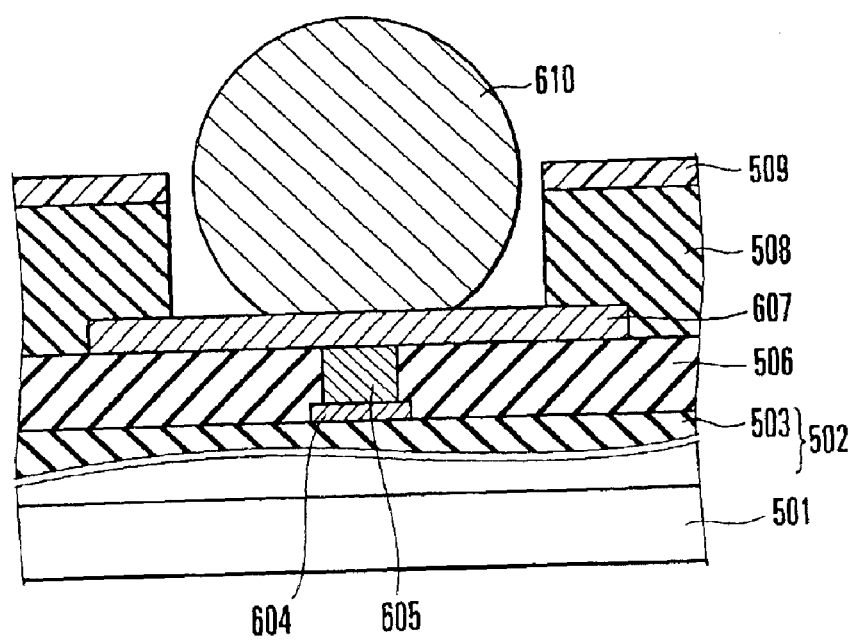
FIG. 6 is a schematic sectional view showing another region of the surface shape recognition sensor shown in FIG. 5C.

As described above, a fluoroplastic film made of a fluorocarbon material can also be formed on the surface of a surface shape recognition sensor having no ground electrode. Even in a surface shape recognition sensor having no ground electrode as shown in FIG. 5B, a bump 610 serving as an external connection terminal is formed on an outer peripheral portion of the sensor chip, as shown in FIG. 6. In this case as well, as described above, if a surface protective film made of a fluorocarbon material, i.e., a fluoroplastic film, is formed by coating the chip with a coating solution in which a fluorocarbon material that forms a film having a hydrophobic property is dissolved, the formation of a surface protective film on the external connection terminal (bump 610) is suppressed.

This mechanism will be described in more detail below.

Figure 5A:
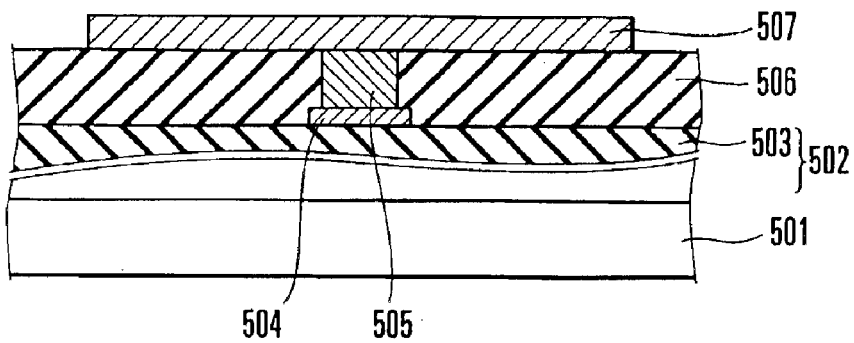
FIG. 5A is a sectional view for explaining a step in a method of manufacturing a surface shape recognition sensor according to the third embodiment of the present invention.

As shown in FIG. 5A, in a surface shape recognition sensor, a multilevel interconnection layer 502 is formed on a semiconductor substrate 501 made of, for example, silicon, and a sensor electrode 507 made of aluminum is formed on the multilevel interconnection layer 502 through an interconnection 504 and connection electrode 505.

The uppermost layer of the multilevel interconnection layer 502 is covered with an insulating film 503. The interconnection 504 is formed on the insulating film 503. The interconnection 504 is covered with an interlayer dielectric film 506 and connected to the sensor electrode 507 through the connection electrode 505 extending through the through hole formed in a portion of the interlayer dielectric film 506. The multilevel interconnection layer 502 is formed from a plurality of elements such as MOS transistors and a plurality of interconnections which connect them to each other, and forms a sensor circuit and the like. The sensor electrode 507 is connected to these circuits through the interconnection 504 and connection electrode 505.

The sensor electrode 507 is formed by forming an aluminum film having a thickness of about 0.5 $\mu$m on the entire surface of the interlayer dielectric film 506 by sputtering after the formation of the connection electrode 505, and processing the film by a known photolithographic technique and etching technique.

After the sensor electrode 507 is formed in this manner, as shown in FIG. 5B, an insulating protective film 508 serving as a capacitance film is formed on the interlayer dielectric film 506 so as to cover the sensor electrode 507. For example, the insulating protective film 508 can be formed by forming a polyimide film made of a polyimide material included in CRC-8300 series available from SUMITOMO BAKELITE to a thickness of about 1 $\mu$m by a coating technique and setting the film by heating it at about 300° C.

Figure 5C:
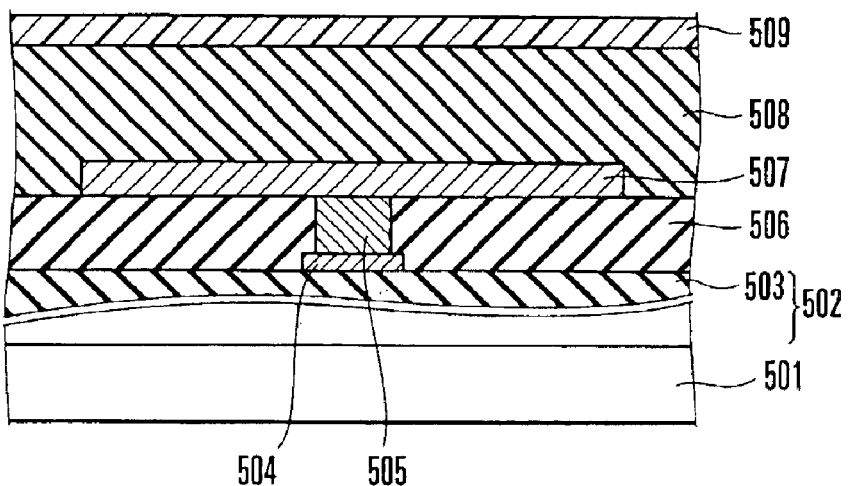
FIG. 5C is a sectional view for explaining a step following the step in FIG. 5B in the method of manufacturing a surface shape recognition sensor according to the third embodiment of the present invention.

A fluoroplastic film 509 made of a fluorocarbon material is then formed on the insulating protective film 508 (FIG. 5C). A method of forming the fluoroplastic film 509 will be described below. First of all, AF 1600 is dissolved in Fluorinert FC-75 (solvent) available from 3M to form a saturated solution of AF 1600 at a room temperature of 23.5° C. This saturated solution will be referred to as a Teflon® saturated solution hereinafter.

When a saturated solution is formed in the above manner, this saturated solution is applied onto the insulating protective film 508 by spin coating. The resultant structure is heated in an atmosphere at 170° C. for 5 min. The resultant structure is then annealed in a nitrogen atmosphere at 300° C. for 1 hr. As a result, the fluoroplastic film 509 can be formed, as shown in FIG. 5C.

In addition, an external connection electrode 607 is formed in a predetermined region such as an outer peripheral portion of the chip so as to be connected, through a connection electrode 605, to an interconnection 604 connected to one of the circuits formed on the multilevel interconnection layer 502. The bump 610 made of gold is formed on the external connection electrode 607. In these regions as well, the fluoroplastic film 509 is formed on the insulating protective film 508. In contrast to this, as described above, almost no fluoroplastic film is formed on the bump 610.

Note that a plurality of sensor chips (surface shape recognition sensors) are simultaneously formed on the semiconductor substrate 501 serving as a semiconductor wafer, a detection surface constituted by a plurality of sensor electrodes 507 is formed on each sensor chip, and each detection surface is protected by the insulating protective film 508 and fluoroplastic film 509. FIG. 5C shows part of this structure.

As described above, only a thin Teflon® film exhibiting poor adhesion can be formed on gold. Even if, therefore, the fluoroplastic film 509 is formed by spin coating, almost no film is formed on the bump 610. For example, a Teflon® solution obtained by diluting a Teflon® saturated solution at a mixing ratio of 1:1 is applied, by spin coating at 1,000 rpm, to a wafer on which a plurality of sensor chips, on each of which components up to the insulating protective film 508 are formed, are simultaneously formed. The resultant structure is heated in an atmosphere at 170° C. and annealed in a nitrogen atmosphere at 300° C. for 30 min to form Teflon® films (fluoroplastic films 509).

As a result, a Teflon® film having a thickness of about 200 to 300 nm is formed, with good adhesion, on the insulating protective film 508 on which a plurality of sensor electrodes 507 are arranged, but almost no Teflon® film is formed on the bump 610. Even if a Teflon® film is formed on the bump 610, the film thickness is about 10 nm as indicated by Table 1 and the film is likely to peel off.

Figure 7:
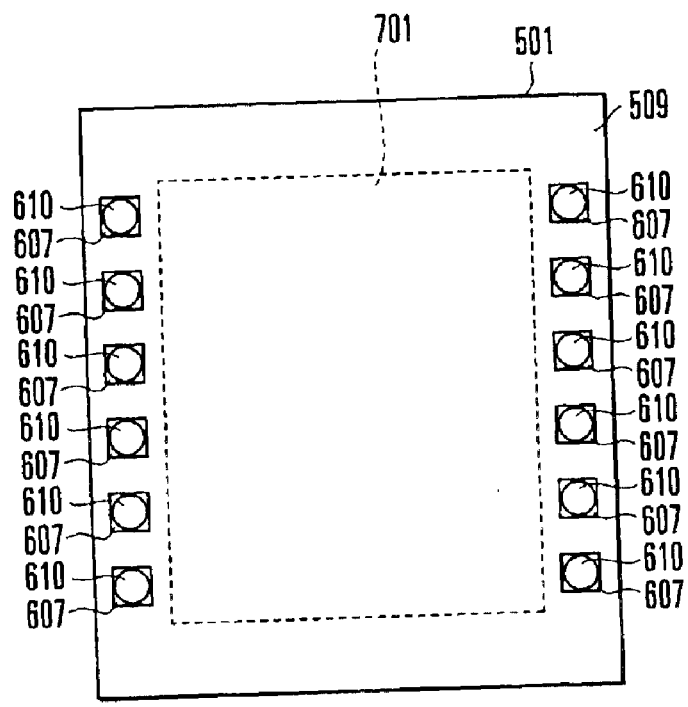
FIG. 7 is a plan view showing the structure of the surface shape recognition sensor shown in FIG. 5C.

Even if, therefore, the fluoroplastic film 509 is formed by applying a Teflon® solution by spin coating, the fluoroplastic film 509 on the bump 610 need not be removed separately, and each sensor chip can be mounted on the mount substrate with electric connection being established. As shown in FIG. 7, a plurality of external connection electrodes 607 and bumps 610 are formed on the outer peripheral portion of a detection region 701 in which the plurality of sensor electrodes of surface shape recognition sensors are arranged.

As has been described above, a surface shape recognition sensor according to the present invention includes a surface protective film which has a hydrophobic property and is formed on the surface of an insulating protective film covering a sensor electrode. This structure prevents substances existing on a detection target from remaining on the surface of the surface protective film after contact of the detection target with the surface protective film. According to the present invention, therefore, a surface shape recognition sensor such as a fingerprint sensor used for authentication or the like acquires excellent effects. For example, it can suppress a deterioration in cleanliness on the detection surface due to residues such as fingerprint residues left on the detection surface which a detection target such as a finger touches, improve the tamper resistance, and suppress a deterioration in detection precision with respect to a surface shape such as a fingerprint.

In addition, in the method of manufacturing a surface shape recognition sensor according to the present invention, after a connection terminal that is exposed on the surface of an insulating protective film is formed, a surface protective film made of a specific material is formed on the insulating protective film by coating it with a coating solution in which a specific material such as a fluorocarbon material that forms a film having a hydrophobic property is dissolved. This makes it possible to prevent a surface protective film from being easily formed on the upper surface (exposed surface) of a connection terminal made of, for example, gold.

What is claimed is:

1. A surface shape recognition sensor comprising:
   a plurality of sensor electrodes arranged in the same plane on a substrate as to be insulated/isolated from each other;
   an insulating protective film which is made of an insulator and formed to over said sensor electrodes;
   capacitance detection means for detecting a capacitance formed by said sensor electrode;
   a surface protective film which has a hydrophobic property and is formed on said insulating protective film;
   a ground electrode which is formed on the substrate such that said ground electrode is partly exposed on surfaces of said insulating protective film and said surface protective film so as to be insulated/isolated from said sensor electrode and come into contact with a surface of a detection target;
   a detection surface which is formed from said plurality of sensor electrode and covered with said insulating protective film and said surface protective film; and
   an external connection terminal formed from a bump structure which is formed on a portion of the substrate which is located around the detection surface and protrudes from an upper surface of said surface protective film,
   wherein said capacitance detection means is configured to detect a capacitance between said ground electrode and each of said sensor electrodes.

2. A sensor according to claim 1, wherein said surface protective film has a lipophobic property.

3. A sensor according to claim 2, wherein said surface protective film peels off by a thickness on the molecular level upon contact of a detection target.

4. A sensor according to claim 2, wherein said surface protective film is made of fluorocarbon.

5. A sensor according to claim 1, wherein said surface protective film is made of polybenzoxazole.

6. A sensor according to claim 5, wherein said insulating protective film and said surface protective film are integrally formed.

7. A surface shape recognition sensor comprising:
   a plurality of sensor electrodes arranged in the same plane on a substrate so as to be insulated/isolated from each other;
   an insulating protective film which is made of an insulator and formed to over said sensor electrodes;

capacitance detection means for detecting a capacitance formed by said sensor electrode;

a surface protective film which has a hydrophobic property and is formed on said insulating protective film;

a ground electrode which is formed on the substrate such that said ground electrode is partly exposed on surfaces of said insulating protective film and said surface protective film so as to be insulated/isolated from said sensor electrode and come into contact with a surface of a detection target, wherein said surface protective film peels off by a thickness on the molecular level upon contact of a detection target, and wherein said surface protective film is made of fluorocarbon, wherein said capacitance detection means is configured to detect a capacitance between said ground electrode and each of said sensor electrodes.

8. A method of manufacturing a surface shape recognition sensor including at least a plurality of sensor electrodes arranged in the same plane on a substrate so as to be insulated/isolated from each other, an insulating protective film which is made of an insulator and formed to cover the sensor electrodes, capacitance detection means for detecting a capacitance formed by the sensor electrode, and a connection terminal exposed on a surface of the insulating protective film, comprising the step of forming a surface protective film made of a specific material, which forms a film having a hydrophobic property, on the insulating protective film by coating the film with a coating solution in which the specific material is dissolved, wherein the specific material is made of fluorocarbon.

9. A method according to claim 8, wherein the surface protective film has a lipophobic property.

10. A method according to claim 9, wherein the surface protective film peels off by a thickness on the molecular level upon contact of a detection target.

11. A method according to claim 8, wherein the surface protective film is made of polybenzoxazole.

12. A method according to claim 8, wherein the connection terminal is a ground electrode which is formed on the substrate such that the ground electrode is partly exposed on surfaces of the insulating protective film and the surface protective film so as to be insulated/isolated from the sensor electrode and come into contact with a surface of a detection target.

13. A method of manufacturing a surface shape recognition sensor including at least a plurality of sensor electrodes arranged in the same plane on a substrate so as to be insulated/isolated from each other, an insulating protective film which is made of an insulator and formed to cover the sensor electrodes, capacitance detection means for detecting a capacitance formed by the sensor electrode, and a connection terminal exposed on a surface of the insulating protective film, comprising the step of forming a surface protective film made of a specific material, which forms a film having a hydrophobic property, on the insulating protective film by coating the film with a coating solution in which the specific material is dissolved, wherein the connection terminal is an external connection terminal form from a bump structure which is formed on a portion of the substrate which is located around detection surface formed from the plurality of sensor electrodes and covered with the insulating protective film and the surface protective film so as to protrude from an upper surface of the surface protective film, wherein the method further comprises the mounting step of connecting the external connection terminal to a connection portion formed on another substrate by an eutectic reaction after the insulating protective film is formed, and wherein in the mounting step, the external connection terminal is connected to the connection portion by a TAB scheme.

* * * * *